(12) United States Patent
Lejeune et al.

(10) Patent No.: US 8,497,488 B2
(45) Date of Patent: Jul. 30, 2013

(54) BELL-SHAPED PROTECTION SYSTEM FOR A DEVICE FOR TREATING ELECTRON-BEAM CONTAINERS

(75) Inventors: Philippe Lejeune, Quimper (FR); Philippe Macquet, Quimper (FR)

(73) Assignee: HEMA, Quimper (FR)

( * ) Notice: Subject to any disclaimer, the term of this patent is extended or adjusted under 35 U.S.C. 154(b) by 0 days.

(21) Appl. No.: 13/519,177

(22) PCT Filed: Dec. 27, 2010

(86) PCT No.: PCT/EP2010/070747
§ 371 (c)(1),
(2), (4) Date: Jun. 26, 2012

(87) PCT Pub. No.: WO2011/080245
PCT Pub. Date: Jul. 7, 2011

(65) Prior Publication Data
US 2012/0273694 A1  Nov. 1, 2012

(30) Foreign Application Priority Data

Dec. 29, 2009  (FR) ........................ 09 59655

(51) Int. Cl.
*H01J 37/20* (2006.01)
(52) U.S. Cl.
CPC ..................... *H01J 37/20* (2013.01)
USPC .......................... 250/455.11; 422/22; 422/186
(58) Field of Classification Search
USPC ........................... 250/455.11; 422/22, 24, 186
See application file for complete search history.

(56) References Cited

U.S. PATENT DOCUMENTS

| 4,944,132 | A | 7/1990 | Carlsson et al. |
| 6,191,424 | B1* | 2/2001 | Stirling et al. ........... 250/455.11 |
| 6,690,020 | B2 | 2/2004 | Loda |
| 7,520,108 | B2* | 4/2009 | Kristiansson et al. ......... 53/426 |
| 2008/0073549 | A1 | 3/2008 | Avnery |
| 2009/0045350 | A1 | 2/2009 | Humele et al. |
| 2012/0279177 | A1* | 11/2012 | Macquet ....................... 53/426 |
| 2013/0001434 | A1* | 1/2013 | Lejeune et al. .......... 250/455.11 |

FOREIGN PATENT DOCUMENTS

| DE | 4407183 A1 | 9/1995 |
| JP | 2003121597 A | 4/2003 |
| JP | 2004069456 A | 3/2004 |

\* cited by examiner

*Primary Examiner* — Kiet T Nguyen
(74) *Attorney, Agent, or Firm* — Bachman & LaPointe, P.C.

(57) ABSTRACT

A treatment device includes one or more treatment stations each including an electron-beam emitter and supporting device for supporting a container beneath the emitter, the emitter being capable of emitting an electron beam passing through the upper opening of a container supported by the supporting means, so as to sterilize the container, and a protection system for stopping the radiation emitted by the emitter(s). The protection system includes an upper portion connected to the emitter, lower portion connected to the supporting device and a moving device capable of moving the upper portion relative to the lower portion, between a retracted position and at least one operative position in which the portions from a protective enclosure in which the emitter and container are positioned.

11 Claims, 3 Drawing Sheets

BELL-SHAPED PROTECTION SYSTEM FOR A DEVICE FOR TREATING ELECTRON-BEAM CONTAINERS

BACKGROUND

This invention relates to a processing device for the sterilisation of containers by electron beam, said device being provided with a particular protection system.

It is known, in particular by U.S. Patent 2009/0045350, devices for treatment comprising a rotating carrousel comprising a rotating support plate supporting a plurality de treatment stations arranged with regular angular spacing, each treatment station comprising sterilising means which comprise an electron-beam emitter, and supporting means for supporting a container under said emitter, said emitter being able to emit an electron beam passing through the upper opening of a container supported by said supporting means, in order to sterilise the container, in particular the internal wall of said container.

In relation to a conventional sterilisation chemically, the sterilisation by electron beam is more effective in terms of sterilisation, faster, and does not leave residual traces after treatment.

Electron-beam emitters however produce undesirable radiation, in particular X rays, and therefore require the provision of protective systems or shielding in order to prevent any risk of propagation of radiation towards the exterior, and as such protect the operators. The protective systems are formed by a protective enclosure made from a lead base, wherein is placed the rotating carrousel for the sterilisation, as well as the infeed and delivery starwheels of the containers. Such protection systems are complex, bulky, and very expensive.

SUMMARY OF THE INVENTION

The purpose of this invention is to propose a processing device for the sterilisation of containers before filling, aiming to overcome the aforementioned disadvantages, which is of high performance and rapid, while still remaining simple in design and implementation.

To this effect, this invention proposes a processing device comprising one or several treatment stations for the sterilisation of containers by electron beam, each treatment station comprising sterilising means which comprise an electron-beam emitter, and supporting means to support a container under said emitter, said emitter being able to emit an electron beam passing through the upper opening of a container supported by said supporting means in order to sterilise said container, in particular the internal wall of the container, and a protection system for stopping the radiation emitted by the emitter or emitters, characterised in that said protection system comprises, for each treatment station, an upper portion assembled to the emitter, a lower portion assembled to the supporting means, and moving means able to carry out a relative movement of the upper portion in relation to the lower portion between a retracted position wherein the upper portion is separated from the lower portion, in order to allow the positioning under the emitter of a container supported by the supporting means, and at least one active position wherein the upper portion and the lower portion form a protective enclosure wherein are positioned the emitter and the container supported by the supporting means, in order to carry out the operations of sterilisation.

According to the invention, the sterilisation is carried out by electron beams and the protection system comprises, for each emitter a lower portion and an upper portion that can be moved toward one another in order to form a protective enclosure, with the same upper portion and/or the same lower portion able to be common to several emitters or to all of the emitters of the device. In relation to enclosures encompassing the entire device, the protective enclosure according to the invention is simple in design and production, less expensive and less cumbersome.

According to an embodiment, said upper portion comprises a first small plate or first plate, referred to as upper, whereon is mounted the emitter, said emitter extending downwards, the lower portion comprises a second small plate, or second plate, referred to as lower, constituting said supporting means, with at least the upper portion or the lower portion comprising a skirt or tubular wall formant with its plate a bell.

According to an embodiment, the upper portion has the form of a bell formed of the upper plate and of a tubular wall, with the lower plate of the lower portion being arranged in the bell when the upper portion is in an active position. Advantageously, the lower plate has a tubular wall extending downwards, and able to slide in the tubular wall of the upper portion, with the overlapping of these tubular walls guaranteeing a blocking of the radiation emitted by the emitter or emitters.

According to an embodiment, said emitter is provided with a tubular nozzle, extending substantially vertically under the upper plate and able to deliver via its distal end the electron beam created by the emitter, said nozzle able to be introduced into said container by passing through the upper opening of the latter during the movement of the upper portion towards the active position. According to an embodiment, said moving means are able to move the upper portion between a first operative position wherein the distal end of the nozzle is arranged above the upper opening of the container and an extreme operative position wherein said nozzle extends into the container.

According to another embodiment, one of the portions of the protection system is in the form of a bell, said bell coming substantially to press via its free edge against the plate of the other portion. According to another embodiment, the upper portion and the lower portion are each formed of a bell, the two bells coming substantially to press against one another in a single active position, or more preferably are partially nested one in the other in operative positions.

According to an embodiment, said device is a device of the linear type, with step-by-step operation, comprising at least one or several channels or parallel treatment lines, for example from 1 to 12 lines, more preferably from 6 to 12 lines, each line being provided with at least one treatment station. According to an embodiment, the processing device comprises several lines parallel to one another, at least one row of treatment stations comprising a treatment station for each treatment line, the upper portion of the protection system comprising an upper plate supporting all of the emitters of said row of treatment stations and a tubular wall extending downwards from said upper plate and surrounding all of said emitters of the row, the lower portion of the protection system comprising a lower plate, able to support at least one container for each treatment line, constituting the supporting means of the treatment stations of said row, said moving means able to move said upper plate and/or the lower plate, more preferably the upper plate.

The protection system comprises the same bell and the same lower plate associated for all of the treatment stations of the row of treatment stations.

The device can include at least two successive rows of treatment stations, parallel to one another. In this case, the protection system comprises more preferably an upper portion, in particular a bell, and a lower portion for each row of treatment stations, in such a way as to form a protective enclosure for each row of treatment stations.

According to another embodiment, the device is of the rotating type, and comprises a carrousel comprising an upper rotating plate, supporting a plurality of treatment stations arranged with regular angular spacing, the protection system comprising an upper portion and a lower portion for each treatment station.

Advantageously, the elements constituting the protection system are made from a lead base.

The sterilisation via electron beam can generate a small quantity of ozone in the enclosure, in particular in the container placed in the enclosure. According to an embodiment, said protection system comprises injection means able to inject a product, into the enclosure, and in particular into the container, during and/or after the irradiation via electron beam, in order to expel the ozone generated during the irradiation by the electron-beam emitter, and as such prevent any deterioration via the ozone of the filling product which will be conditioned in the container. The injected product is a gaseous product or a liquid product with a low boiling point, in particular a neutral gas such as nitrogen, or liquid nitrogen. Advantageously, said injection means include an injection tube, extending more preferably along the nozzle of the emitter, said tube able to be introduced into said container by passing through the upper opening of the latter during the movement of the upper portion towards the active position.

According to an embodiment, said protection system, more preferably the upper portion of the protection system, and in particular the upper plate, comprises evacuating means, for the evacuation towards the exterior of the enclosure of the gas contained in the enclosure, in order to prevent any overpressure in the enclosure during the relative movement of the upper portion in relation to the lower portion and/or during the injection of a neutral gas in the enclosure. Said evacuating means include for example one or several vent holes, more preferably arranged in the wall of the upper portion of the protection system, and in particular in the upper portion of the protection system, each vent hole being more preferably provided with an external pipe placed in a partial vacuum.

According to an embodiment, said protection system further comprises a system of baffles in order to act as a screen to the radiation emitted by the emitter or emitters at the connection between the upper portion and the lower portion, said system of baffles comprising for example an annular edge of the lower tubular wall, extended by an annular wall, the upper tubular wall inserted into the housing formed between the annular wall and the lower tubular wall when the bell is in active position.

BRIEF DESCRIPTION OF THE DRAWINGS

The invention shall be better understood, and other purposes, details, characteristics and advantages shall appear more clearly during the following detailed explanatory description of a particular currently preferred embodiment of the invention, in reference to the annexed diagrammatical drawings, wherein.

DETAILED DESCRIPTION OF THE PREFERRED EMBODIMENT(S)

Figure 1:
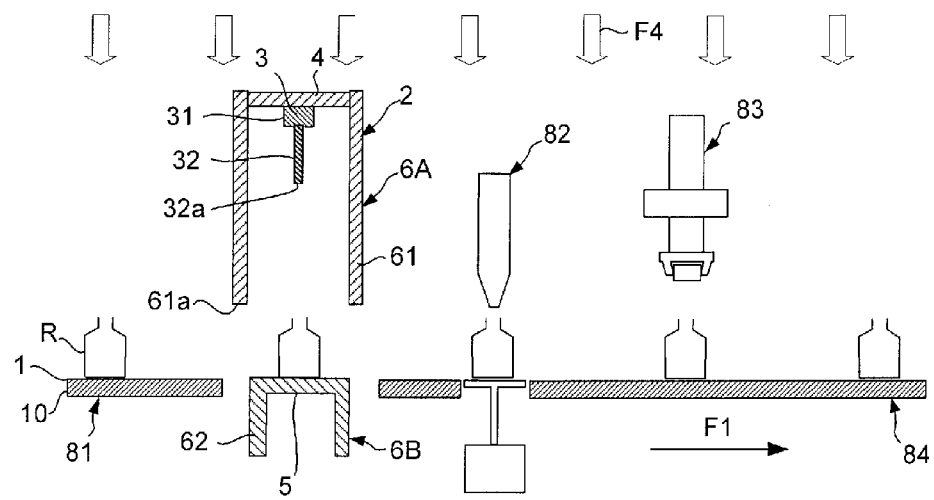
FIG. 1 is a diagrammatical side view of a processing device according to the invention comprising a treatment station for the sterilisation of containers.

FIG. 1 shows a processing device for the sterilisation of containers R, the filling of containers processed with a filling product and the closing of containers.

The processing device comprises a treatment line 1 comprising a system of conveying 10 with step-by-step operation, along which are arranged from upstream to downstream in relation to the forward direction F1, a station 81 for bringing containers, a treatment station 2 for the sterilisation of containers, a filling station 82, a closing station 83, and an evacuation station 84 for the containers. In order to guarantee a sterile filling of the containers, the entire treatment line is placed under a laminar flow of sterile air, for example a descending laminar flow, such as is shown diagrammatically by the arrows F4.

The device according to the invention allows for the sterilisation, filling and corking of any type of container R comprising an upper main opening. The treatment station 2 allows for the sterilisation of the interior wall of the containers, by passing through the upper opening of the containers. The filling station 82, known per se, for example of the weight-based type, allows for the filling of sterilised containers with a determined quantity of filling product, with the filling product being liquid or viscous, for example a liquid product such as water, milk or fruit juice. The closing station 83 or corking station here makes it possible to install a cap on the upper opening of the filled containers.

The treatment station 2 comprises sterilisation means 3 formed by an electron-beam emitter 31, known per se, provided with a tubular nozzle or tubular antenna 32, of extended form, the emitter being able to deliver an electron beam via the distal end 32a of its nozzle. The distal end of the nozzle is provided with a sheet of titanium. The sterilising means are for example formed by an emitter such as described in U.S. Patent document 2008/0073549. The emitter is mounted fixed onto the lower surface of a small plate or plate 4 referred to as upper, its nozzle, with longitudinal vertical axis A (FIG. 2A), extending vertically downwards. The nozzle is defined in such a way that it can be inserted by the upper opening of the containers in order to irradiate the interior of the containers. In reference to FIG. 2A, the plate support is mounted mobile on the chassis C of the device, by the intermediary of the moving means 9, also called means of raising/lowering, known per se, making it possible to move the upper plate in vertical translation, such as shown by the arrow F2, between a high retracted position, and low operative positions described hereinafter.

Each treatment station further comprises supporting means of a container R for the maintaining of a container under the emitter, substantially centred according to the axis A of the nozzle. The supporting means include a harness or plate 5 referred to as lower, mounted fixed onto the chassis C of the device, able to support a container. Alternatively, the moving means act on the supporting means, with the upper bell being mounted fixed onto the chassis.

The device according to the invention comprises a protection system or shielding in order to stop the radiation emitted by the emitters, in particular the interference radiation of the X ray type. This system of shielding comprises an upper portion 6A and a lower portion 6B. The upper portion has the shape of a bell 6A formed by the upper plate 4 and an upper tubular wall 61, also called an upper skirt, extending downwards from said upper plate. The upper plate constitutes the bottom wall of the bell, the upper skirt 61 surrounds the emitter 31 and its antenna 32 and extends beyond the distal end 32a of the antenna. The lower portion 6B is formed by said lower plate 5 and by a lower tubular wall 62, also called lower skirt, extending downwards from said lower plate 5. The device comprises for example a single treatment line 1, with a single treatment station 2 for the sterilisation. The protective bell 6A has a general cylindrical shape, with its upper plate 4 having the shape of a disc, and its upper skirt 61 having a circular transversal section. The lower plate 5 also has the shape of a disc and its lower skirt 62 has a circular section of which the outside diameter substantially corresponds to the inside diameter of the upper skirt 61.

Figures 2A, 2B, 2C:
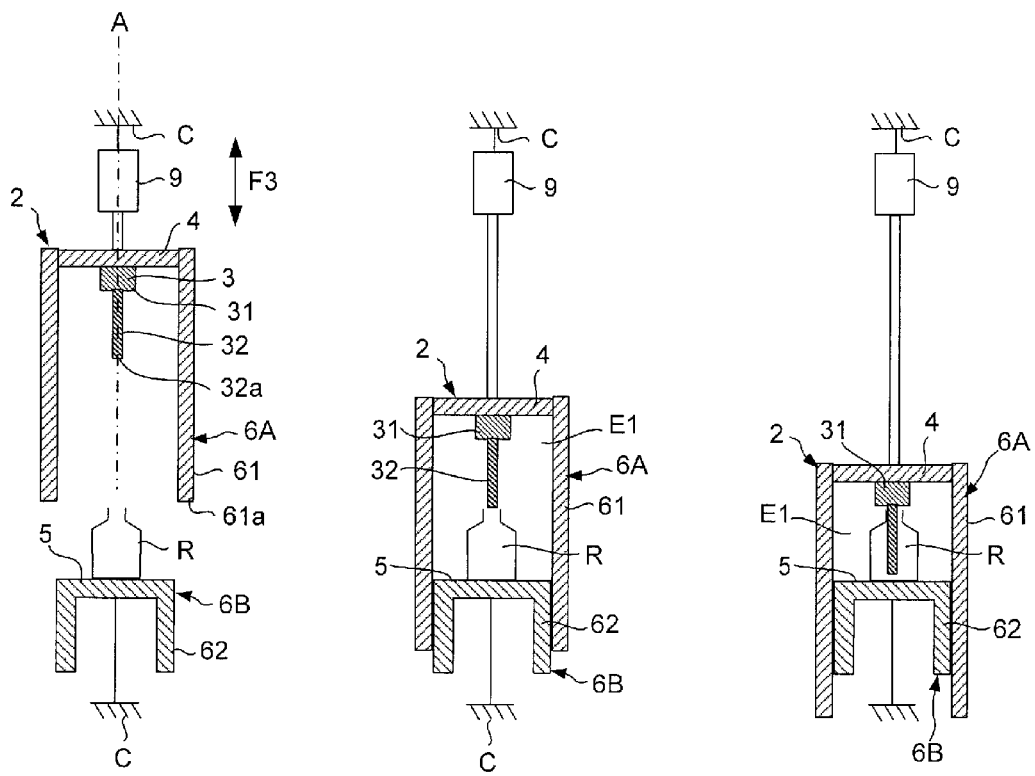
FIGS. 2A to 2C are side views of the treatment station showing the various positions of the protection system during the sterilisation of a container.

In reference to FIG. 2a, in the high retracted position of the upper plate, the annular free edge 61a of the bell 6A is arranged above the lower plate 5, in such a way that a container R can be brought on said lower plate, under the emitter and under the bell.

For the sterilisation operation of a container, the upper plate 4 is moved in vertical translation downwards, via the moving means 9, towards a first operative position, shown in FIG. 2B. During this movement, the bell 6A comes to cover the container R, the lower skirt 62 of the lower portion sliding in the upper skirt 61 of the bell. The emitter 31 and its antenna 32 are arranged above the opening of the container. The upper plate 4 and the upper skirt 61 forming the bell 6A, as well as the lower plate 5 provided with its lower skirt 62, are made from a lead base, and together form in this first operative position a protective enclosure E1. In this first operative position, the emitter 31 can be activated in order to irradiate the external wall of the container. The upper skirt 61 and the lower skirt 62 overlap over a height that is sufficient to prevent any radiation from exiting the enclosure E.

The upper plate 4 is then moved further downwards, via the moving means 9, to the extreme operative position shown in FIG. 2C, in order to irradiate the entire internal wall of the container. During this movement, the lower skirt 62 of the lower portion slides in the upper skirt 61 of the bell. The length of the nozzle 32 and the height of the upper skirt 61 are adapted, in such a way that the distal end 32a of the nozzle is arranged in the vicinity of the bottom of the container R in the extreme operative position.

The upper plate 4 is then progressively brought back towards its first low operative position shown in FIG. 2B. The irradiation is then stopped, and the upper plate 4 is brought back to its retracted position shown in FIG. 2A. The conveyor 10 is then activated to evacuate the treated container and transfer it towards the filling station 82, and to bring another container to be treated under the emitter.

The device according to the invention can be used for the sterile filling of different containers at a level of sterilisation of a magnitude of Log 3.

The containers can be of the bottle type, such as shown diagrammatically in the figures, made of glass or of a plastic material such as PET, PEHD or PP. The filling is carried out at the filling station 82 by means of a filling spout, and the bottle is closed again, more preferably under a nitrogen-saturated atmosphere, at the corking station 83 which comprises screwing means of a cap. According to an embodiment, the bottle is filled by means of two parallel tubes which are inserted into the bottle and which are used to deliver different products. A first tube is used to deliver for example a liquid, such as a fruit juice, with the other tube being used to deliver pulp and/or vitamins for example.

The containers can be cartons of the <<brick>> type, conventionally formed of a complex carton/LDPE/Aluminium material. The cartons are preformed beforehand and transferred open in the device. The cartons are open on their lower side, or on their upper side which is possible provided with a capsule base, heat-sealed to the complex material and whereon a capsule is screwed. After sterilisation via insertion of the antenna into the container via its open side, the cartons are filled at the filling station by the use of a filling spout or of one or two tubes, then are sealed at the closing station, more preferably under a nitrogen-saturated atmosphere, with the screwing means being replaced with block of heating irons.

The containers can be cartons of the <<Brick>> type, preformed beforehand and already closed via heat-sealing at the upper portion, with a capsule base, of 32 or 36 mm for example, already heat-sealed to the complex material. The cartons are transferred into the device with the base open, without the capsule. After sterilisation by insertion of the antenna into the container via the open base, the filling is carried out with a tube, then the closing is carried out by screwing the capsule on the base.

The containers can be tins, made of steel or aluminium, which are crimped after filling, with the closing station thus comprising a crimping unit.

Figure 3:
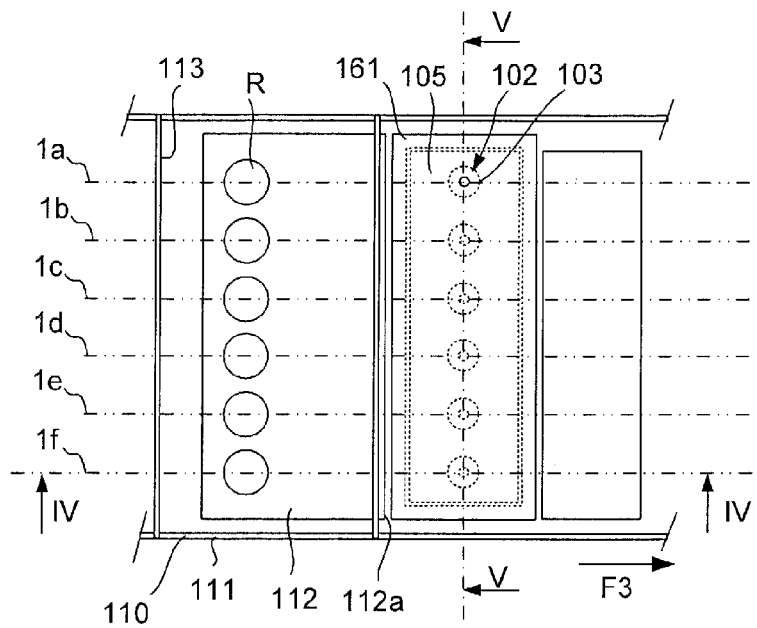
FIG. 3 is a diagrammatical top view of a processing device according to an alternative embodiment, comprising several sterilisation stations in parallel.
Figure 4:
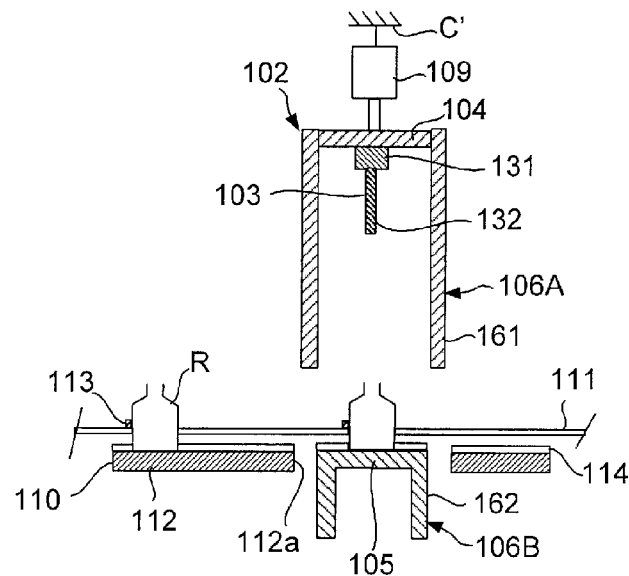
FIG. 4 is a diagrammatical view according to the section plane IV-IV in FIG. 3.
Figure 5:
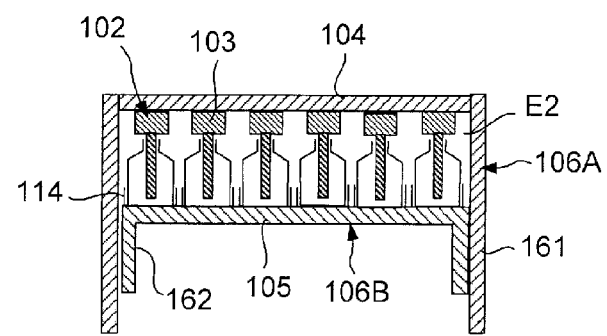
FIG. 5 is a diagrammatical view according to the section plane V-V in FIG. 3.

FIGS. 3 to 5 show an alternative embodiment wherein the device comprises 6 parallel treatment lines 1a-1f, each treatment line comprising a treatment station 102 for the sterilisation of containers, with the stations arranged according to a row perpendicular to the treatment lines.

The emitters 131 are mounted on the lower surface of the same upper plate 104, formed for example by a rectangular. The upper plate is mounted mobile in translation on the chassis C' of the device. A common lower plate 105, formed of a rectangular plate constitutes the supporting means for all of the treatment stations 2 of the row of treatment stations.

The upper portion of the protection system is formed of a bell 106A, constituted by said common upper plate 104 and a tubular wall or upper skirt 161, of rectangular section. The lower portion 106B of the protection system is formed by said common lower plate 05 and a tubular wall or lower skirt 162 extending downwards.

Moving Means 109 (FIG. 3), common to the various treatment stations, make it possible to move the upper plate 104 between a retracted position shown in FIG. 4, and operative positions, such as described hereinabove, and in particular an extreme operative position shown in FIG. 5, in order to form a protective enclosure E2 and allow six containers to be sterilised simultaneously.

The driving of the containers R along the 6 treatment lines is provided by a conveyor belt 110 with cleats, comprising two endless belts 111 arranged on either side of a transport slider bed 112, wherein between are mounted cleats 113. The slide bed 112 has an opening 112a for the positioning of the lower plate and the passage of the tubular wall 162 of the bell.

Longitudinal guide lips 114 (FIG. 5) are advantageously provided on the slider bed and the lower plate to transversally guide the containers along treatment lines 1a-1f. Alternatively, the transversal guiding of the containers is provided by the cleats, the cleats comprising for example imprints of which the shape corresponds to that of the containers to be conveyed.

In order to bring a row of containers on the lower plate 105, the upper plate is brought to high retracted position, and the conveyor is actuated to move the cleats in the direction F3 and as such push a row of containers under the emitters, such as shown in FIG. 4. The conveyor is then actuated in the reverse direction to move the cleats towards the rear and in particular separate the opening 112a from the cleat that pushed the containers under the emitters so as to allow for the movement of the bell 106A towards its operative positions.

Each line of the device can also include, downstream of the treatment station 102, a filling station and a corking station such as described hereinabove.

Alternatively, each treatment line 1a-1f comprises several treatment stations arranged according to several rows perpendicular to the treatment lines. For each row of treatment stations, the protection system comprises a bell of which the common upper plate supports the emitters of the stations of the row, and a lower portion of which the lower plate constitutes the supporting means of the stations of the row. The bells are more preferably moved between their retracted position and their active position by the common moving means 109. The rows of treatment stations are shifted from one another in order to allow for the positioning of a cleat between two successive bells when the bells are in active position.

The protection system according to the invention can also be used with devices for treatment of the rotating types comprising a carrousel comprising a support plate or upper plate, in the form of an annular or circular plate, intended to be mounted rotating about a fixed frame around a vertical axis of rotation. The support plate supports a plurality of treatment stations arranged with regular angular spacing around the axis of rotation. Each station comprises an emitter mounted on the lower surface of the plate. The upper portion of the protection system is constituted by the support plate and a plurality of upper skirts surrounding the emitters and extending from the lower surface of the plate. Each upper skirt forms with the upper plate a bell associated with a treatment station. The supporting means of each treatment station include a harness or lower plate provided with a lower skirt. Each treatment station comprises moving means acting here on the lower plate in order to move it between a separated position from the upper plate in order to allow for the positioning of a container on the lower plate and the removal of a container from the lower plate, for example by means of an infeed starwheel and of a delivery starwheel, and operative positions wherein the lower plate with its upper skirt forms with the upper bell a protective enclosure.

Figure 6:
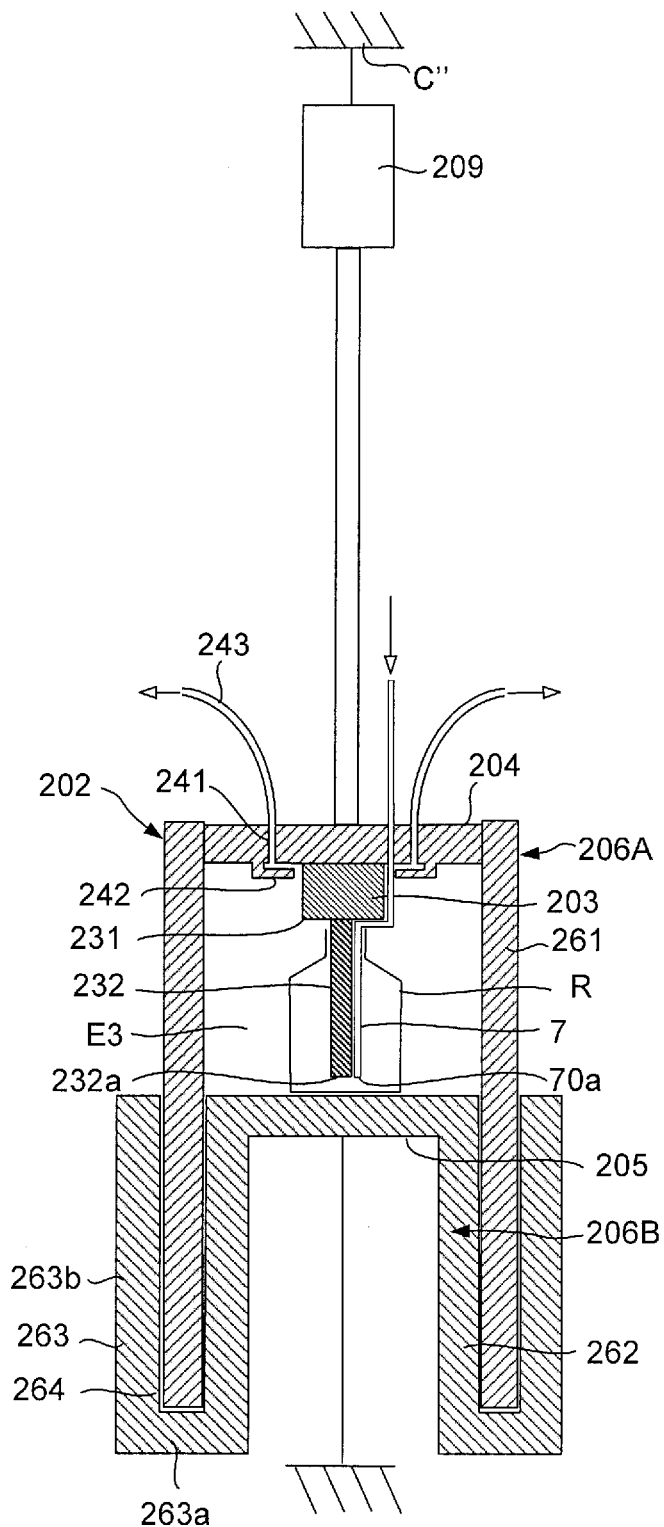
FIG. 6 is a diagrammatical side view of a treatment station according to an alternative embodiment.

FIG. 6 shows an alternative embodiment of a treatment station which is differentiated from that shown in FIGS. 2A to 2C by the fact that it comprises injection means for the injection of a product into the enclosure, in order to expel the ozone generated during the sterilisation via electron beam, and evacuating means for the evacuation of gas outside of the enclosure. The treatment station 202 comprises as previously sterilisation means 203 comprising an electron-beam emitter 231, provided with a tubular antenna 232, and mounted on an upper plate 204. The protection system comprises an upper bell 206A formed by the upper plate 204 and an upper tubular wall 261, and a lower portion 206B formed by a lower plate 205, provided with a lower tubular wall 262. The upper plate is able to be moved in vertical translation by moving means 209, and the lower plate, used as a support for the containers R, is mounted fixed onto the chassis C".

The treatment station comprises a tubing or injection tube 7 mounted fixed in the bell. This tube extends parallel to the antenna of the emitter, with the distal end 70a of the tube being arranged substantially at the same level as the distal end 232a distal of the antenna. This tube passes in a substantially sealed manner through the upper plate 204 of the bell. The tube is used to inject into the container R a neutral gas, such as nitrogen, immediately after the irradiation, for example when the upper plate 4 is in its first operative position, in order to create an overpressure in the container R and as such expulse outside of the container the ozone generated by the irradiation. Alternatively, the injection of neutral gas is also carried out during the irradiation, for example when the upper plate is moved from its extreme operative position towards its first operative position.

Alternatively, the tube is used to deliver into the container R liquid nitrogen, for example a drop of liquid nitrogen, during and/or just after irradiation, with the liquid nitrogen passing to gaseous phase then progressively filling the container and progressively flushing the ozone outside of the container.

The upper plate 204 is provided with vent holes 341 emerging into the enclosure E3 in order to prevent an overpressure inside the enclosure. These vent holes are used to evacuate the gas which is contained in the enclosure and which is compressed during the descent of the upper plate 204 until its extreme operative position. Moreover, these vent holes are used to evacuate the ozone generated in the container by the irradiation and pushed outside of the container R via the nitrogen injected. A system of baffles 242, made of lead, is provided on the lower surface of the upper plate in order to act as a screen to the X rays generated during the irradiation, and as such prevent any propagation of radiation outside of the enclosure via said vent holes. The vent holes are connected to flexible pipes 243, placed in a partial vacuum, in order to suck the gas compressed by the relative movement of the bell and of the lower portion, and in particular the ozone generated by the irradiation.

Advantageously, a system of baffles 263, also made of lead, is provided in order to prevent any propagation of radiation on the interface between the upper portion 206A and the lower portion 206B, more precisely at the interface between the upper tubular wall 261 of the bell, and the lower tubular wall 262. The system of baffles 263 comprises a horizontal annular edge 263a extending towards the exterior from the free edge of the lower tubular wall 262, and extending via a vertical annular wall 263b, which extends upwards parallel to the lower tubular wall, substantially to the lower plate 205. This annular wall 263b forms with the lower tubular wall 262 an annular housing 264 wherein slides the upper tubular wall 261 of the bell during the relative movement of the bell in relation to the lower plate 205.

Although the invention has been described in liaison with a particular embodiment, it is of course obvious that it is in no way limited to it and that it includes all of the technical equivalents of the means described as well as combinations therein if the latter fall within the scope of the invention.

The invention claimed is:

1. Processing device comprising
at least one treatment station for the sterilization of containers via electron beams, each said treatment station comprising sterilization means which comprise an electron-beam emitter provided with a tubular nozzle and supporting means for supporting a container under said emitter, said emitter able to emit an electron beam passing through an upper opening of a container supported by said supporting means in order to sterilize said container, and
a protection system in order to stop radiation emitted by the emitter,
wherein said protection system comprises, for each said treatment station,
an upper portion assembled to the emitter, said upper portion having a shape of a bell formed from a first plate and from a tubular wall, said emitter being mounted on said first plate and said tubular nozzle extends substantially vertically under the first plate,
a lower portion comprising a second plate, constituting said supporting means, and
moving means able to carry out a relative movement of the upper portion in relation to the lower portion between a retracted position wherein the upper portion is separated from the lower portion, in order to position under the emitter of a container supported by the supporting means, and operative positions wherein the upper portion and the lower portion form a protective enclosure wherein are positioned the emitter and the container supported by the supporting means, the second plate being arranged in the bell when the upper portion is in an active position, said moving means able to move the upper portion between a first operative position wherein a distal end of the tubular nozzle is arranged above an upper opening of the container and an extreme operative position wherein said tubular nozzle extends in the container.

2. Processing device according to claim 1, wherein the second plate has a tubular wall extending downwards, able to slide in the tubular wall of the upper portion.

3. Processing device according to claim 1, wherein said device is a device of the linear type, with step-by-step operation, comprising at least one or several parallel treatment lines, each treatment line being provided with at least one treatment station.

4. Processing device according to claim 3, wherein:
several of said treatment lines are arranged parallel to each other,
at least one row of treatment stations comprising a treatment station for each treatment line,
the first plate of the bell supporting all of the emitters of said row of treatment stations and the tubular wall of the bell extending downwards from said first plate and surrounding all of said emitters of the row,
the second plate constituting the supporting means of the treatment stations of said row, and
said moving means able to move said first plate and/or the second plate.

5. Processing device according to claim 1, wherein said device is of the rotating type and comprises a carrousel having an upper rotating plate supporting a plurality of treatment stations arranged with regular angular spacing, and the protection system comprising an upper portion and a lower portion for each treatment station.

6. Processing device according to claim 1, wherein elements constituting the protection system are made from a lead base.

7. Processing device according to claim 1, wherein said protection system comprises injection means able to inject a product into the enclosure in order to expel ozone generated during irradiation by the electron-beam emitter.

8. Processing device according to claim 7, wherein said injection means include an injection tube, said injection tube able to be introduced into said container by passing through the upper opening of the container during movement of the upper portion towards the active position.

9. Processing device according to claim 1, wherein said protection system comprises evacuation means for the evacuation towards an exterior of the enclosure of the gas contained in the enclosure.

10. Processing device according to claim 1, wherein said protection system comprises a system of baffles to act as a screen to radiation emitted by the emitter at the connection between the upper portion and the lower portion.

11. Processing device according to claim 10, wherein said system of baffles comprises an annular edge of a lower tubular wall, extending via an annular wall, the upper tubular wall being inserted into a housing formed between the annular wall and the lower tubular wall when the bell is in active position.

* * * * *